United States Patent [19]
Hamade et al.

[11] Patent Number: 5,770,188
[45] Date of Patent: Jun. 23, 1998

[54] GLUCOXIDE DERIVATIVES FOR ENZYME MODIFICATION, LIPID-COATED ENZYMES, METHOD OF PRODUCING SUCH ENZYMES AND ANTIFOULING PAINT COMPOSITION

[75] Inventors: Ryoji Hamade, Kadoma; Naoki Yamamori, Tuzuki-gun; Yoshio Okahata, Kawasaki, all of Japan

[73] Assignee: Nippon Paint Co., Ltd., Osaka, Japan

[21] Appl. No.: 742,597

[22] Filed: Oct. 28, 1996

[30] Foreign Application Priority Data

Oct. 26, 1995 [JP] Japan .................................... 7-278709
Oct. 26, 1995 [JP] Japan .................................... 7-278718
Oct. 26, 1995 [JP] Japan .................................... 7-278722

[51] Int. Cl.[6] .................................................... A61K 31/74
[52] U.S. Cl. ........................... 424/78.09; 106/16; 106/17; 106/18.32; 504/173; 514/625; 514/629; 564/201; 564/203
[58] Field of Search ................ 424/78.09; 564/201, 564/203; 106/16, 17, 18, 32; 514/625, 629; 504/173; 554/61

[56] References Cited

U.S. PATENT DOCUMENTS

4,849,227  7/1989  Cho .......................................... 424/498
5,374,665  12/1994  Isaka et al. .............................. 523/122

OTHER PUBLICATIONS

Yukagaku (1995), vol. 44, No. 3, pp. 179–183. Ohkatsu et al., Glycolipid Enzyme Models.
Chem. Abs. No. 122:234176 and the compounds having registry No. 162019–55–8, 163854–13–5, 163854–14–6, 1995.
Inada et.al., Bichem and Biophys. res. Commun, vol. 122, No. 2, pp. 845–850, 1984.

*Primary Examiner*—Shailendra Kumar
*Attorney, Agent, or Firm*—Pollock, Vande Sande & Priddy

[57] ABSTRACT

This invention is related to glucoxide derivatives for enzyme modification of the following general formula (1), to provide a lipid-coated enzyme showing high activity in organic solvents; antifouling paint compositions containing a lipid-coated enzyme being stable in organic solvents by coating with a $C_6$ to $C_{30}$ lipid, and a paint resin, to be capable of forming paint films having good antifouling activity and durability and allowing an enzyme to retain good stability in the paint and in paint films; and self-polishing antifouling paint compositions containing an enzyme-susceptible resin and a lipid-coated enzyme capable of catalyzing the degradation of said resin and being stable in organic solvents by coating with a $C_6$ to $C_{30}$ lipid, to retain the antifouling effect for a prolonged period of time without adversely affecting the environment.

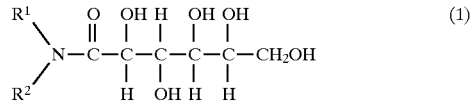

12 Claims, No Drawings

GLUCOXIDE DERIVATIVES FOR ENZYME MODIFICATION, LIPID-COATED ENZYMES, METHOD OF PRODUCING SUCH ENZYMES AND ANTIFOULING PAINT COMPOSITION

TECHNICAL FIELD

The present invention relates to glucoxide derivatives for enzyme modification, lipid-coated enzymes coated with said glucoxide derivatives for enzyme modification, and, a method of producing lipid-coated enzymes using said derivatives.

The present invention further relates to an antifouling paint composition, in particular, which comprises at least one enzyme being stable in organic solvents by coating with a lipid.

BACKGROUND ART

Advances in the knowledge of excellent characteristics of enzymes in recent years have increased the demand for efficient utilization thereof in the field of high technology, for example organic synthesis of physiologically active substances and development of novel functional paints.

However, although enzymes catalyze various reactions in aqueous solution, they are generally unstable in organic solvents and readily aggregate, resulting in deactivation. Therefore, enzymes are not fully utilized in the field in which organic solvents are used.

So far, several methods have been proposed for carrying out reactions in organic solvents while maintaining enzyme activity. Thus, for instance, there may be mentioned the reversed micellar system (Luisi et al., J. Am. Chem. Soc., 106, 7285, 1984) and the surface modified enzyme with polyethylene glycol (Y. Inada et al., Biochem. Biophys. Res. Commun., 122, 845, 1984). However, these methods have drawbacks; the stability of enzyme activity is very poor and the procedure is complicated. There is also a method of stabilizing enzymes in organic solvents which comprises causing formation of a lipid-coated enzyme (Japanese Kokai Publication Sho-64-80282). This method, too, has problems, for example in that the synthetic lipid is difficult to prepare and the activity of the lipid-coated enzyme obtained is low.

Meanwhile, antifouling paints have so far been used to prevent organisms from attaching to marine structures. However, the antifouling paints generally contain, as antifouling compositions, toxic compounds such as tributyltin oxide, derivatives thereof or like heavy metal compounds and therefore produce adverse effects on the environment.

Antifouling paints generally contain an antifouling composition and an elution controlling additive such as rosin, and the antifouling paint films release the antifouling composition together with the elution additive, with the paint binder resin remaining without change. Therefore, the amount of the antifouling composition sustainedly released decreases with the lapse of time. Formation of a skeleton layer which is derived from the resin as a residue on the paint film surface restricts the permeation of seawater through paint films, worsening the sustained release property of the antifouling composition and thereby causing rapid deterioration of the antifouling property.

As antifouling paints maintaining the antifouling property for a prolonged period of time by sustainedly releasing a constant amount of an antifouling composition over a long period of time, there are known the so-called self-polishing antifouling paints with which the paint binder resin is consumed from the paint surface.

However, the so-far known antifouling paints of this type are environment-unfriendly since an organotin polymer is hydrolyzed by seawater to thereby release a toxic organotin compound constantly as an antifouling composition.

In recent years, attention has been focused on the use of enzymes, which have low toxicity, as antifouling compositions in antifouling paint compositions.

For example, Japanese Kokai Publications Hei-02-227465, Hei-02-227471 and Hei-04-252284 disclose antifouling paint compositions containing proteolytic enzymes such as proteases.

In the paint compositions disclosed therein, however, the enzymes invariably have poor stability in paints and in paint films and are readily inactivated. Therefore, the paint films formed are poor in antifouling property and lacking in durability of said property. It is also a problem that the procedure for preparation is complicated.

The present invention is to solve the prior art problems mentioned above. Thus, it is an object of the present invention to provide a lipid-coated enzyme showing high activity in organic solvents. Another object is to provide an antifouling paint composition capable of forming paint films having good antifouling activity and durability and allowing an enzyme to retain good stability in the paint and in paint films. A further object is to provide a self-polishing antifouling paint composition with which the antifouling property is retained for a prolonged period of time without adversely affecting the environment.

SUMMARY OF THE INVENTION

The glucoxide derivative for enzyme modification as provided by the present invention is represented by the following general formula (1):

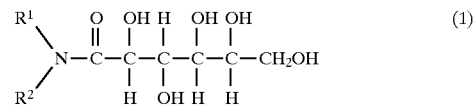

wherein $R^1$ and $R^2$ each independently represents a hydrocarbon group having 6 to 20 carbon atoms.

The antifouling paint composition according to the present invention contains a lipid-coated enzyme which is stable in organic solvents as a result of coating with a lipid having 6 to 30 carbon atoms, and a paint resin.

Furthermore, the self-polishing antifouling paint composition according to the present invention contains an enzyme-susceptible resin and a lipid-coated enzyme which is stable in organic solvents as a result of coating with a lipid having 6 to 30 carbon atoms and capable of catalyzing the degradation of said resin.

DETAILED DESCRIPTION OF THE INVENTION

The glucoxide derivative for enzyme modification of the present invention is represented by said general formula (1). Preferably, each $R^1$ and $R^2$ in said general formula (1) independently is selected from the group consisting of an alkyl group having 6 to 20 carbon atoms and an alkenyl group having 6 to 20 carbon atoms.

The glucoxide derivative for enzyme modification as provided by the present invention can be readily synthesized by reacting a $R^1$, $R^2$-substituted secondary amine, for example, a dialkyl-substituted secondary amine, with glucono-1,5-lactone. Generally, the reaction is carried out by dissolving said amine and lactone in a solvent having a boiling point in the range of 60° to 250° C., for example, methanol, and heating the solution under reflux.

Said glucoxide derivative for enzyme modification renders various enzymes, which are intrinsically hydrophilic and unstable in an organic solvent, stable in an organic solvent by coating them. The method of coating is not limited to any particular one but, generally, it comprises the step of dissolving the above-mentioned glucoxide derivative for enzyme modification in a hydrophilic solvent to give a solution of the glucoxide derivative for enzyme modification, and the step of adding dropwise said solution of the glucoxide derivative for enzyme modification to a buffer solution containing an enzyme.

The term "hydrophilic solvent" as used herein includes, within the meaning thereof, not only such hydrophilic organic solvents as methanol, ethanol, propanol, acetone and methyl ethyl ketone but also aqueous solutions such as buffer solutions.

For example, 1 mg of an enzyme is dissolved in 0.02 to 20.0 ml, preferably 0.1 to 2 ml, of a buffer solution with a pH of 4.0 to 9.0 and, at 0° to 30° C., preferably with cooling at 4° C., a glucoxide derivative solution is added dropwise to the enzyme solution with stirring. The glucoxide derivative solution preferably prepared by dissolving the glucoxide derivative in a hydrophilic solvent using said solvent generally in an amount of 0.002 to 0.1 ml, more preferably in an amount of 0.005 to 0.02 ml, per milligram of the glucoxide derivative.

Stirring can be effected using an ordinary stirring device such as a propeller or blade mixer, magnetic stirrer or homomixer. Dropwise addition with sufficient stirring and cooling results in precipitation of the glucoxide derivative-coated enzyme. This precipitate is collected by centrifugation or filtration, washed with a buffer solution and then with distilled water, and either subjected as such to freeze drying, fluidized bed drying, or spray drying after dispersed in a small amount of distilled water, whereby the glucoxide derivative-coated enzyme which is stable in an organic solvent can be obtained as a powder.

In the above procedure, the glucoxide derivative is used preferably in a weight ratio, relative to the enzyme weight, of 0.2 to 100, more preferably 0.5 to 10. When said ratio is less than 0.2, the recovery of the glucoxide derivative-coated enzyme becomes low whereas, at a ratio more than 100, the enzyme activity decreases.

As the enzyme capable of being rendered stable in an organic solvent by the method of the present invention, there may be mentioned hydrolases, oxidoreductases, transferases, lyases, isomerases and synthetases, among others.

The hydrolases include esterases and lipases hydrolyzing esters (produced by microorganisms or derived from animal organs or sera or from plant tissues, seeds, etc.) and biotissues containing the same; proteases and peptidases hydrolyzing peptide bonds, such as animal organ-derived pepsins, chymotrypsins, carboxypeptidases, thermolysins, cathepsins and aminopeptidases, plant tissue-derived papains, chymopapains, bromelins and aminopeptidases, and microorganism-derived carboxypeptidases, proteinases and dipeptidases; glucosidases hydrolyzing glucoside bonds, such as α- and β-glucosidase, α- and β-glucanase, α- and β-galactosidase, α- and β-amylase, cellulase and pullulanase; phosphatases hydrolyzing phosphate bonds, such as phosphomonoesterases, phosphodiesterases and pyrophosphatases; amidases hydrolyzing amido groups, such as arginase, urease and glutaminase; nucleases, collagenases and so forth.

Specific examples of the oxidoreductases are alcohol dehydrogenase, lactate dehydrogenase, glucose oxidase, chollesterol oxidase and amine oxidases, among others.

In addition, transferases such as transphosphorilases, transglucosidases, transpeptidases, transamidases and transglutaminase; elimination-causing enzymes such as decarboxylases and lyases; isomerases such as racemases and isomerases; and synthetases such as ligases can also be used in the practice of the present invention.

The antifouling paint composition of the present invention contains a lipid-coated enzyme rendered stable in organic solvents by coating with a lipid having 6 to 30 carbon atoms, and a paint resin.

As said lipid-coated enzyme, there may be mentioned hydrolases such as proteolytic enzymes and polysaccharide decomposing enzymes. By using such enzymes, proteins and polysaccharides, which are involved in the mechanisms of attachment of marine organisms, can be degraded, so that said organisms can be prevented from attaching. Said enzymes may also degrade cell walls of attaching organisms and thereby achieve attachment prevention.

As said proteolytic enzymes, there may be mentioned proteases and peptidases hydrolyzing peptide bonds, for instance animal organ-derived pepsins, trypsins, chymotrypsins, carboxypeptidases, thermolysins, cathepsins and aminopeptidases, plant tissue-derived papains, chymopapains, bromelins and aminopeptidases, and microorganism-derived carboxypeptidases, proteinases and dipeptidases.

Said polysaccharide decomposing enzymes include glucosidases hydrolyzing glucoside bonds, for example α- and β-glucosidase, amyloglucosidase, α- and β-glucanase, α- and β-galactosidase, α- and β-amylase, glucoamylase, cellulase, chitinase, chitosanase, pectinase and lysozyme.

The term "lipid" as used herein means a compound having a long-chain alkyl group, which is a hydrophobic group, and a hydrophilic group.

The lipid to be used in the practice of the present invention may be a natural one or a synthetic one. It preferably has 6 to 30 carbon atoms. With shorter lipids, desired modification of enzyme characteristics is difficult to attain, while longer lipids render lipid-coated enzymes difficult to carry out their enzyme functions. Said lipid should preferably have a hydrophilic moiety selected from the group consisting of sugar residues, phosphoric acid groups, sulfonic acid groups and ammonium salt groups, since these groups can readily bind to hydrophilic groups on the enzyme surface and give good stability to the lipid-coated enzymes.

The natural lipid may be a neutral one or an ionic one. For instance, the neutral lipid includes, among others, glyceroglycolipids such as monogalactosyldiglycerides and galactosylglucosyldiglycerides, sphingoglycolipids such as monoglucosylceramides, ceramide hexosides and gangliosides, steroid glycosides such as sterol glycosides, cardenolid glycosides and saponins, as well as fatty acids such as diacyltrehaloses and triacylglucoses. As anionic lipids, there may be mentioned such phospholipids as phosphatidylinositols, phosphatidylglycerols and phosphatidic acids. As amphoteric lipids, there may be mentioned such phospholipids as phosphatidylcholines, phosphatidylethanolamines and phosphatidylserines.

Usable as the synthetic lipid are synthetic bilayer-forming compounds, for example sorbitan monopalmitate, sorbitan monostearate, sorbitan dipalmitate, sorbitan distearate, ethylene glycol dipalmitate, ethylene glycol distearate, polyoxyethylene dipalmitate and polyoxyethylene distearate, mono- and dialkylphosphates, mono- and dialkyl type polyethylene glycols, mono- and dialkyl sulfosuccinates, mono- and dialkyl type glycolipids as well as mono- and dialkylammonium salts.

Lipids represented by the general formula (1) given above are also preferred for use in the practice of the present invention, since the enzymes coated therewith are superior in stability in organic solvents.

The antifouling paint composition of the present invention is prepared by incorporating, in a paint composition, an enzyme rendered stable in an organic solvent by coating with said lipid.

According to a method of coating an enzyme with the lipid, for instance, the enzyme is dissolved in a buffer solution with a pH of 4.0 to 9.0, and the lipid is added dropwise to the solution with stirring at 0° to 30° C., preferably with cooling. For dropwise addition, the lipid is generally dissolved in a small amount of methanol, ethanol, propanol, acetone, methyl ethyl ketone or some other hydrophilic organic solvent, or in a buffer solution.

For stirring, propeller or blade mixers, magnetic stirrers, homomixers or like stirring apparatus may also be used. The lipid-coated enzyme is caused to precipitate by stirring with sufficient cooling. The precipitate is collected by centrifugation or filtration, washed with a buffer solution and then with distilled water, and subjected to freeze drying or fluidized bed drying to give the lipid-coated enzyme in a powder form.

The mixing ratio (lipid/enzyme), on the solid weight basis, between the lipid and enzyme is preferably within the range of 0.2/1 to 100/1, more preferably within the range of 0.4/1 to 10/1. When the ratio is less than 0.2/1, no coated-enzyme formation can result, whereas at ratios more than 100/1, the enzyme activity will become too low. The buffer solution for dissolving the enzyme is used, for example, in an amount of 0.02 to 20.0 ml per mg of the enzyme. When the lipid is to be dissolved in a solvent, 0.002 to 0.1 ml, for instance, of a hydrophilic organic solvent may be used per mg of the lipid.

The enzyme stabilized in organic solvents in the above manner can retain its activity and remain stable for a prolonged period of time in such organic solvents as toluene, xylene, butyl acetate, methyl isobutyl ketone (MIBK) and n-butanol. Therefore, said enzyme can be incorporated into various organic solvent-based paint compositions and water-based paint compositions so far used in preparing antifouling paint compositions by any method per se known in the field of paint manufacture. Such enzymes produce excellent antifouling effects even after paint film formation from the resulting paint compositions.

The lipid-coated enzyme is contained in the antifouling paint composition in an amount such that the weight ratio between the lipid-coated enzyme and paint resin (lipid-coated enzyme/paint resin) falls within the range of 0.00001/1 to 1/1, preferably 0.0001/1 to 0.1/1, more preferably 0.001/1 to 0.01/1. When said weight ratio is less than 0.00001/1, the enzyme activity in the resin is too low for the effects of the enzyme to be expected. When it is more than 1/1, the resin characteristics are lost.

The paint resin to be used in the antifouling paint composition of the present invention is not limited to any particular species but may be any one known in the art. Preferred examples are resins for organic solvent paints, such as vinyl chloride resins, chlorinated rubber type resins, chlorinated polyethylene resins, chlorinated polypropylene resins, acrylic resins, styrene-butadiene resins, polyester resins, epoxy resins, polyamide resins, petroleum resins, silicone resins, silicone rubber resins, waxes, paraffins, rosin esters and rosin type resins, and resins for water paints, such as acrylic emulsion resins, epoxy emulsion resins and vinyl acetate resins. These may be used either alone or as a mixture of two or more.

Furthermore, one or more of those plasticizers, color pigments, extenders, solvents and other additives that are generally used in paint compositions may be incorporated each in the antifouling paint composition of the present invention in an amount in ordinary use.

The above-mentioned antifouling paint composition, when, in said composition, the paint resin is an enzyme-susceptible resin and the lipid-coated enzyme is capable of degrading said enzyme-susceptible resin, constitutes the self-polishing antifouling paint composition of the present invention.

The term "enzyme-susceptible resin" as used herein means a resin capable of being degraded by the action of an enzyme to, at least, segments due to the cleavage of chemical bonds in the resin.

The enzyme-susceptible resin to be used in the self-polishing antifouling paint composition of the present invention is not limited to any particular species but may be any one known in the art to be usable as a paint resin. Thus, for example, it includes, among others, such polyester resins as alkyd resins, polycaprolactone, polyvalerolactone and polyethylene adipate, and such polyamino acid resins as polylysine, polyglutamic acid and poly-$\epsilon$-aninocaproyl-$\alpha$-alanine. Natural polysaccharides such as cellulose, starch, chitin and alginic acid as well as derivatives thereof may also be used. These may be used either singly or in combination as a mixture of two or more.

In the self-polishing antifouling paint composition, an enzyme-susceptible resin and a non-enzyme-susceptible resin known in the art as a paint resin may be used in combination.

In that case, the enzyme-susceptible resin and non-enzyme-susceptible resin may be used as a mixture or in the form of a copolymer. The weight ratio between the non-enzyme-susceptible resin and the enzyme-susceptible resin (non-enzyme-susceptible resin/enzyme-susceptible resin) is generally within the range of 100/1 to 0/1, preferably 20/1 to 0/1, more preferably 10/1 to 0/1.

Examples of such non-enzyme-susceptible resin are organic solvent paint resins such as vinyl chloride resins, chlorinated rubber resins, chlorinated polyethylene resins, chlorinated polypropylene resins, acrylic resins, styrene-butadiene resins, polyester resins, epoxy resins, polyamide resins, petroleum resins, silicone resins, silicone rubber resins, waxes, paraffins, rosin ester resins and rosin type resins, and water paint resins such as acrylic emulsion resins, epoxy emulsion resins and vinyl acetate resins. These may be used either singly or in combination.

The enzyme to be used in the self-polishing antifouling paint composition of the present invention is to be selected depending on the enzyme-susceptible resin used therein. Thus, the enzyme should be capable of hydrolyzing the enzyme-susceptible resin employed in the environment of about 5° to 35° C. in seawater. By incorporating such enzyme causing cleavage of chemical bonds of said enzyme-susceptible resin to degrade the binder resin in the antifouling paint composition, it becomes possible for the paint film surface to be renewed constantly and for the sustained antifouling composition release to be controlled. As a result, a constant amount of the antifouling composition can be released sustainedly for a prolonged period of time. Therefore, it is also possible to use an antifouling composition of low toxicity.

When the enzyme-susceptible resin is a polyester resin, lipases and esterases can be used, preferably in the case of polylactone, lipase can be used, and when said resin is a polyamino acid resin, proteases, peptidases and the like can be used. In the case of cellulose and derivatives thereof, cellulase and the like can be used. In the case of starch and derivatives thereof, α-amylase, β-amylase, glucoamylase and the like can be used. In the case of chitin and derivatives thereof, chitinase and the like can be used and, in the case of alginic acid, alginate lyase and the like can be used. The origin of the enzyme is not limited provided that it can degrade the enzyme-susceptible resin.

The glucoxide derivatives for enzyme modification provided by the present invention can be synthesized in an easier and simpler manner as compared with the conventional modifier lipids and can be obtained in large quantities at low cost. Furthermore, lipid-coated enzymes obtained by using said glucoxide derivatives can retain a higher level of enzyme activity in organic solvents as compared with the prior art ones.

The antifouling paint compositions of the present invention are excellent in enzyme stability in paints and in paint films and can form paint films excellent in antifouling activity and durability thereof.

The self-polishing antifouling paint compositions of the present invention can retain their antifouling activity over a prolonged period of time without adversely affecting the environment.

EXAMPLES

The following examples illustrate the present invention in further detail but are by no means limitative of the scope of the present invention.

Production Examples 1 to 6 illustrate the preparation of lipids 1 to 6, which are glucoxide derivatives for enzyme modification.

Production Example 1
Preparation of lipid 1

A reaction vessel equipped with a condenser, a stirrer and a nitrogen inlet tube was charged with 35 g of 1,5-gluconolactone, 57 g of dilaurylamine and 125 ml of methanol, and the mixture was heated under reflux for 2 hours. The thus-formed light-yellow solid was extracted with n-hexane using a Soxhlet extracator, whereby 45 g of a white solid was obtained. This white solid gave an IR spectrum lacking the 1,5-gluconolactone ester peak at 1750 $cm^{-1}$. Hereinafter, this substance is called lipid 1.

Production Example 2
Preparation of lipid 2

Lipid 2 was prepared in the same manner as in Example 1 except that 62 g of distearylamine was used in lieu of dilaurylamine and heptane in lieu of n-hexane.

Production Example 3
Preparation of lipid 3

Lipid 3 was prepared in the same manner as in Example 1 except that 56 g of cocoamine was used in lieu of dilaurylamine.

Production Example 4
Preparation of lipid 4

Lipid 4 was prepared in the same manner as in Example 1 except that 61 g of oleylstearylamine was used in lieu of dilaurylamine.

Production Example 5
Preparation of lipid 5

Lipid 5 was prepared in the same manner as in Example 1 except that 52 g of octylpalmitylamine was used in lieu of dilaurylamine.

Production Example 6
Preparation of lipid 6

Lipid 6 was prepared in the same manner as in Example 1 except that 22 g of diethylammine was used in lieu of dilaurylamine.

Example 1

Mucor miehei (filamentous fungus)-derived lipase (100 mg) was dissolved in 50 ml of phosphate buffer solution (0.1M, pH 7.0) and the insoluble matter was removed by centrifugal sedimentation (solution a).

Lipid 1 (100 mg) was dissolved in 1 ml of acetone (solution b). Solution b was added dropwise to solution a with stirring and ice cooling. The resultant mixture was stirred with ice cooling for 4 hours and then allowed to stand overnight at 4° C. This solution containing a precipitate was subjected to centrifugation (4° C., 4,000×g, 10 min.), the supernatant was removed, and the remaining precipitate was washed with phosphate buffer solution and distilled water. Then, this solid was freeze-dried to give 102.4 mg of a powder. The thus-obtained coated enzyme was identified by UV spectrometry.

Example 2

Rhizopus niveus (filamentous fungus)-derived lipase (100 mg) was used in lieu of Mucor miehei-derived lipase used in Example 1 and was dissolved in 50 ml of phosphate buffer solution (0.1M, pH 7.0) and the insoluble matter was removed by centrifugal sedimentation to give solution a. Then, 100 mg of lipid 2 was dissolved in 1 ml of acetone (solution b). Thereafter, the procedure of Example 1 was followed to give 91.6 mg of a coated enzyme in powder form.

Example 3

A coated enzyme in powder form (88.9 mg) was obtained in the same manner as in Example 1 except that 100 mg of lipid 3 was used in lieu of lipid 1.

Example 4

A coated enzyme in powder form (97.6 mg) was obtained in the same manner as in Example 1 except that 100 mg of lipid 4 was used in lieu of lipid 1.

Example 5

A coated enzyme in powder form (92.4 mg) was obtained in the same manner as in Example 1 except that 100 mg of lipid 5 was used in lieu of lipid 1.

Comparative Example 1

Didodecyl glutamate gluconamide (100 mg) was used in lieu of the glucoxide derivative used in Example 1 and was dissolved in 1 ml of acetone to give solution b. Thereafter, the procedure of Example 1 was followed to give 105.2 mg of a powder.

Comparative Example 2

Monogalactosyl diglyceride (100 mg) was used in lieu of the glucoxide derivative used in Example 2 and was dissolved in 1.5 ml of acetone to give solution b. Thereafter, the procedure of Example 2 was followed to give 52.6 mg of a powder.

Comparative Example 3

The procedure of Example 1 was followed using 100 mg of lipid 6 in lieu of lipid 1. No powder-form coated enzyme was obtained.

Example 6
Activity measurement of lipid-coated enzymes

Each 1 mg of the coated enzymes obtained in Examples 1 to 5 and Comparative Examples 1 to 3 were dissolved in 5 ml of toluene for lipase activity measurement. A 100-$\mu$l portion of each coated enzyme-containing toluene solution was added to an olive oil-polyvinyl alcohol emulsion and, after 30 minutes of reaction at 37° C., the free fatty acid formed was quantitated by titration with 0.05N aqueous potassium hydroxide solution (JIS K 0601, 1988, Method of alkali titration of free fatty acids using olive oil as a substrate). One unit of lipase activity (IU) is defined as the activity causing formation of 1 $\mu$ mol of free fatty acid in one minute at 37° C. The thus-determined activities of the coated enzymes are shown below in Table 1.

TABLE 1

|  | Lipase activity (U/mg) |
| --- | --- |
| Example 1 | 87.6 |
| Example 2 | 81.5 |
| Example 3 | 82.3 |
| Example 4 | 84.7 |
| Example 5 | 78.4 |
| Comparative Example 1 | 22.4 |
| Comparative Example 2 | 24.3 |
| Comparative Example 3 | — |

The results shown above indicate that the glucoxide derivative-coated enzymes of the present invention have higher enzyme activity than the prior art ones.

Preparation Example 2-1

Bacillus subtilis-derived protease (10 g) was dissolved in 5 liters of phosphate buffer solution (0.1M, pH 7.0) and the insoluble matter was removed by centrifugal sedimentation to give solution a. Didodecyl glutamate gluconamide (nonionic lipid; 10 g) was dissolved in 100 ml of acetone to give solution b. Solution b was added dropwise to solution a with stirring and ice cooling. Then, stirring was continued for 4 hours with ice cooling, followed by overnight standing at 4° C. The precipitate-containing solution was subjected to centrifugation (4° C., 4,000×g, 10 min.), the supernatant was removed, and the precipitate was washed with phosphate buffer solution and distilled water. Then, this solid was subjected to freeze-drying to give 3.7 g of lipid-coated enzyme 2-1 as a powder. The thus-obtained lipid-coated enzyme 2-1 was identified by UV spectrometry.

Preparation Example 2-2 to 2-8

Lipid-coated enzymes 2-2 to 2-8 were prepared in the same manner as in Preparation Example 2-1 except that the combination of enzyme and lipid was varied as indicated below in Table 2.

TABLE 2

|  | Preparation Example | | | | | | | |
| --- | --- | --- | --- | --- | --- | --- | --- | --- |
|  | 2-1 | 2-2 | 2-3 | 2-4 | 2-5 | 2-6 | 2-7 | 2-8 |
| Amount of enzyme (g) | | | | | | | | |
| Protease (*B. subtilis*) | 10 | — | — | 10 | 10 | 10 | 10 | 10 |
| Chitinase (Bacillus sp.) | — | 10 | — | — | — | — | — | — |
| Lysozyme (chicken egg white) | — | — | 10 | — | — | — | — | — |
| Amount of lipid (g) | | | | | | | | |
| Didodecyl glutamate gluconamide | 10 | 10 | 10 | 40 | 5 | 2 | — | — |
| Sorbitan monopalmitate | — | — | — | — | — | — | 10 | — |
| Phosphatidylcholine | — | — | — | — | — | — | — | 10 |

Example 2-1

Lipid-coated enzyme 2-1 (5 g), 30 g of vinyl chloride-vinyl isopropyl ether copolymer "Laroflex MP-45" (trade name, product of BASF), 25 g of natural rosin "WW Rosin" (trade name, product of Arakawa Chemical Industries), 25 g of xylene and 15 g of methyl isobutyl ketone were placed in a vessel and the mixture was treated for dispersion at 5,000 rpm for 15 minutes using a high-speed Disper mixing device to give an antifouling paint composition. The thus-obtained paint composition was applied, to a dry film thickness of 60 to 80 $\mu$m, to test steel panels (300×100 mm) coated in advance with an anticorrosive paint and then dried for 1 day to give antifouling paint-coated steel panels.

Examples 2-2 to 2-12 and Comparative Examples 2-1 to 2-6

Antifouling paint compositions were prepared in the same manner as in Example 2-1 except that the compositions shown in Tables 3 and 4 were used.

TABLE 3

| | Example | | | | | | | | | | | |
| --- | --- | --- | --- | --- | --- | --- | --- | --- | --- | --- | --- | --- |
| Amount (g) | 2-1 | 2-2 | 2-3 | 2-4 | 2-5 | 2-6 | 2-7 | 2-8 | 2-9 | 2-10 | 2-11 | 2-12 |
| Lipid-coated enzyme 2-1 | 5 | — | — | — | — | — | — | — | 1 | 0.1 | 5 | 7 |
| Lipid-coated enzyme 2-2 | — | 25 | — | — | — | — | — | — | — | — | — | — |
| Lipid-coated enzyme 2-3 | — | — | 5 | — | — | — | — | — | — | — | — | — |
| Lipid coated enzyme 2-4 | — | — | — | 15 | — | — | — | — | — | — | — | — |
| Lipid-coated enzyme 2-5 | — | — | — | — | 5 | — | — | — | — | — | — | — |
| Lipid-coated enzyme 2-6 | — | — | — | — | — | 10 | — | — | — | — | — | — |
| Lipid-coated enzyme 2-7 | — | — | — | — | — | — | 5 | — | — | — | — | — |

TABLE 3-continued

|  | Example | | | | | | | | | | | |
| --- | --- | --- | --- | --- | --- | --- | --- | --- | --- | --- | --- | --- |
| Amount (g) | 2-1 | 2-2 | 2-3 | 2-4 | 2-5 | 2-6 | 2-7 | 2-8 | 2-9 | 2-10 | 2-11 | 2-12 |
| Lipid-coated enzyme 2-8 | — | — | — | — | — | — | — | 5 | — | — | — | — |
| Laroflex MP-45[a] | 30 | 30 | 30 | 30 | 30 | 30 | 30 | 30 | 30 | 30 | 55 | 30 |
| WW Rosin[b] | 25 | 10 | 25 | 25 | 25 | 25 | 25 | 25 | 25 | 25 | — | 15 |
| Curous oxide | — | — | — | — | — | — | — | — | — | — | — | 10 |
| Xylene | 25 | 25 | 25 | 25 | 25 | 25 | 25 | 25 | 27 | 28 | 25 | 25 |
| Methyl isobutyl ketone | 15 | 15 | 15 | 15 | 15 | 15 | 15 | 15 | 17 | 17 | 15 | 15 |

[a]Vinyl chloride-vinyl isopropyl ether copolymer, product of BASF.
[b]Product of Arakawa Chemical Industries.

TABLE 4

|  | Comparative Example | | | | | |
| --- | --- | --- | --- | --- | --- | --- |
| Amount (g) | 2-1 | 2-2 | 2-3 | 2-4 | 2-5 | 2-6 |
| Protease (B. subtilis) | — | — | 8 | — | — | 8 |
| Chitinase (Bacillus sp.) | — | — | — | 5 | — | — |
| Lysozyme (chicken egg white) | — | — | — | — | 4 | — |
| Laroflex MP-45[a] | 30 | 30 | 30 | 30 | 30 | 30 |
| WW Rosin[b] | 25 | 25 | 15 | 15 | 15 | 15 |
| Cuprous oxide | 5 | — | — | — | — | 10 |
| Xylene | 25 | 28 | 25 | 25 | 25 | 25 |
| Methyl isobutyl ketone | 15 | 17 | 15 | 15 | 15 | 15 |

[a]Vinyl chloride-vinyl isopropyl ether copolymer, product of BASF.
[b]Product of Arakawa Chemical Industries.

Paint film evaluation for antifouling activity

The antifouling paint-coated steel panels were immersed in seawater at the depth of 1 m using a test raft located off the shore of Taniano City, Okayama Prefecture and macroscopically checked at timed intervals for the extent of fouling of the paint film surface by attachment of marine organisms. The results thus obtained are shown below in Table 5 and Table 6. Each numerical value given in Table 5 and Table 6 indicates the percentage of the area fouled with attaching organisms (% fouling). Test steel panels coated with an anticorrosive paint but not with any antifouling paint were simultaneously immersed in the sea as control samples.

Paint stability evaluation

A portion of each paint composition obtained in Examples 2-1, 2-3 and 2-12 and Comparative Examples 2-4, 2-5 and 2-6 was storeded at 25° C. for 1 month, 3 months or 6 months. Each paint after storage was evaluated for antifouling activity in the same manner as mentioned above. The results obtained are shown in Table 7 and Table 8.

TABLE 5

|  | Fouling (%) | | | | | | | | | | | |
| --- | --- | --- | --- | --- | --- | --- | --- | --- | --- | --- | --- | --- |
| Immersion period | Example | | | | | | | | | | | |
| (months) | 2-1 | 2-2 | 2-3 | 2-4 | 2-5 | 2-6 | 2-7 | 2-8 | 2-9 | 2-10 | 2-11 | 2-12 |
| 2 | 0 | 0 | 0 | 0 | 0 | 0 | 0 | 0 | 0 | 0 | 0 | 0 |
| 4 | 0 | 0 | 0 | 0 | 0 | 0 | 0 | 0 | 0 | 0 | 0 | 0 |
| 6 | 0 | 0 | 0 | 0 | 0 | 0 | 0 | 0 | 0 | 0 | 0 | 0 |
| 12 | 0 | 0 | 0 | 0 | 0 | 0 | 0 | 0 | 0 | 5 | 0 | 0 |

TABLE 6

|  | Fouling (%) | | | | | | |
| --- | --- | --- | --- | --- | --- | --- | --- |
| Immersion period | Comparative Example | | | | | | |
| (months) | 2-1 | 2-2 | 2-3 | 2-4 | 2-5 | 2-6 | Control |
| 2 | 40 | 50 | 30 | 25 | 30 | 20 | 50 |
| 4 | 60 | 70 | 60 | 50 | 55 | 50 | 70 |
| 6 | 90 | 100 | 90 | 70 | 70 | 70 | 100 |
| 12 | 100 | 100 | 100 | 100 | 100 | 100 | 100 |

TABLE 7

|  | Fouling (%) | | | | | | | | |
| --- | --- | --- | --- | --- | --- | --- | --- | --- | --- |
| Storage period | Example 2-1 | | | Example 2-3 | | | Example 2-12 | | |
| (months) | 1 | 3 | 6 | 1 | 3 | 6 | 1 | 3 | 6 |
| Immersion period (months) | | | | | | | | | |
| 2 | 0 | 0 | 0 | 0 | 0 | 0 | 0 | 0 | 0 |
| 4 | 0 | 0 | 0 | 0 | 0 | 0 | 0 | 0 | 0 |
| 6 | 0 | 0 | 0 | 0 | 0 | 0 | 0 | 0 | 0 |
| 12 | 0 | 0 | 0 | 0 | 0 | 0 | 0 | 0 | 0 |

TABLE 8

| Storage period | Comparative Example 2-4 | | | Comparative Example 2-5 | | | Comparative Example 2-6 | | |
|---|---|---|---|---|---|---|---|---|---|
| (months) | 1 | 3 | 6 | 1 | 3 | 6 | 1 | 3 | 6 |
| Immersion period (months) | | | | | | | | | |
| 2 | 30 | 50 | 50 | 30 | 50 | 50 | 30 | 50 | 50 |
| 4 | 60 | 70 | 70 | 60 | 70 | 70 | 60 | 70 | 70 |
| 6 | 90 | 100 | 100 | 90 | 100 | 100 | 80 | 100 | 100 |
| 12 | 100 | 100 | 100 | 100 | 100 | 100 | 100 | 100 | 100 |

Fouling (%)

Preparation Example 3-1

*Mucor miehei* (filamentous fungus)-derived lipase (10 g) was dissolved in 5 liters of phosphate buffer solution (0.1M, pH 7.0) and the insoluble matter was removed by centrifugal sedimentation, to give solution a. Solution b was prepared by dissolving 10 g of didodecyl glutamate gluconamide, a nonionic lipid, in 100 ml of acetone. Solution b was added dropwise to solution a with stirring and ice cooling. Stirring was continued for 4 hours with ice cooling, followed by overnight standing at 4° C. The precipitate-containing solution was subjected to centrifugation (4° C., 4,000×g, 10 min.), the supernatant was removed and the precipitate was washed with phosphate buffer solution and distilled water. Then, this solid was subjected to freeze drying to give 8.9 g of lipid-coated enzyme 3-1. The thus-obtained lipid-coated enzyme was identified by UV spectrometry.

Preparation Examples 3-2 to 3-9

Lipid-coated enzymes 3-2 to 3-9 were prepared in the same manner as in Preparation Example 3-1 except that the enzyme-lipid combination was varied as specified in Table 9.

TABLE 9

| | Preparation Example | | | | | | | | |
|---|---|---|---|---|---|---|---|---|---|
| | 3-1 | 3-2 | 3-3 | 3-4 | 3-5 | 3-6 | 3-7 | 3-8 | 3-9 |
| Amount of enzyme (g) | | | | | | | | | |
| Lipase (*Mucor miehei*) | 10 | 10 | 10 | 10 | 10 | — | — | — | — |
| Cellulase (*Trichoderma viride*) | — | — | — | — | — | 10 | 10 | 10 | — |
| Protease (*Bacillus subtilis*) | — | — | — | — | — | — | — | — | 10 |
| Amount of lipid (g) | | | | | | | | | |
| Didodecyl glutamate gluconamide | 10 | — | — | 40 | 2 | 10 | — | — | 10 |
| Sorbitan monopalmitate | — | 10 | — | — | — | — | 10 | — | — |
| Phosphatidylcholine | — | — | 10 | — | — | — | — | 10 | — |

Preparation Example 3-10

Synthesis of alkyd resin a

Soybean oil (50 g), 33.12 g of phthalic anhydride, 19.92 g of trimethylolethane, 0.99 g of pentaerythritol, 0.5 g of dibutyltin oxide and 5 g of xylene were charged into a 500-ml flask and the mixture was maintained at about 140° C. for 6 hours under reflux and bubbling with gaseous nitrogen, to give 99 g of alkyl resin a.

Preparation Example 3-11

Synthesis of polyamino acid resin a

A 500-ml flask was charged with 100 g of poly-L-lysine (molecular weight: about 1,000) and 100 g of oleic acid and the mixture was heated and dehydrated at 160° C. without using any solvent, to give 193 g of poly-L-lysine having oleic acid on side chains, i.e. polyamino acid resin a.

Example 3-1

Lipid-coated enzyme 3-1 (2 g), 40 g of polycaprolactone "Placcel H4" (product of Daicel Chemical Industries), 20 g of cuprous oxide and 38 g of toluene were placed in a vessel and the mixture was treated for dispersion using a high-speed Disper mixer at 5,000 rpm for 15 minutes to give an antifouling paint composition. The thus-obtained paint composition was applied, to a dry film thickness of 60 to 80 μm, to steel-made test panels (300×100 mm) coated beforehand with an anticorrosive paint, and dried for 1 day to give antifouling paint-coated steel panels.

Examples 3-2 to 3-12 and Comparative Examples 3-1 to 3-8

Antifouling paint compositions were prepared in the same manner as in Example 3-1 except that the formulations shown in Tables 10 and 11 were respectively employed.

TABLE 10

| Amount (g) | Example | | | | | | | | | | | |
|---|---|---|---|---|---|---|---|---|---|---|---|---|
| | 3-1 | 3-2 | 3-3 | 3-4 | 3-5 | 3-6 | 3-7 | 3-8 | 3-9 | 3-10 | 3-11 | 3-12 |
| Lipid-coated enzyme 3-1 | 2 | — | — | — | — | — | — | — | 2 | — | 0.2 | 0.05 |
| Lipid-coated enzyme 3-2 | — | 2 | — | — | — | — | — | — | — | — | — | — |
| Lipid-coated enzyme 3-3 | — | — | 2 | — | — | — | — | — | — | — | — | — |

TABLE 10-continued

| Amount (g) | 3-1 | 3-2 | 3-3 | 3-4 | 3-5 | 3-6 | 3-7 | 3-8 | 3-9 | 3-10 | 3-11 | 3-12 |
|---|---|---|---|---|---|---|---|---|---|---|---|---|
| Lipid-coated enzyme 3-4 | — | — | — | 2 | — | — | — | — | — | — | — | — |
| Lipid-coated enzyme 3-5 | — | — | — | — | 2 | — | — | — | — | — | — | — |
| Lipid-coated enzyme 3-6 | — | — | — | — | — | 2 | — | — | — | — | — | — |
| Lipid-coated enzyme 3-7 | — | — | — | — | — | — | 2 | — | — | — | — | — |
| Lipid-coated enzyme 3-8 | — | — | — | — | — | — | — | 2 | — | — | — | — |
| Lipid-coated enzyme 3-9 | — | — | — | — | — | — | — | — | — | 2 | — | — |
| Placcel H4[i] | 40 | 40 | 40 | 40 | 40 | — | — | — | — | — | 40 | 40 |
| Ethylcellulose N-22[ii] | — | — | — | — | — | 40 | 40 | 40 | — | — | — | — |
| Alkyd resin a | — | — | — | — | — | — | — | — | 40 | — | — | — |
| Polyamino acid resin a | — | — | — | — | — | — | — | — | — | 40 | — | — |
| Caprous oxide | 20 | 20 | 20 | 20 | 20 | 20 | 20 | 20 | 20 | 20 | 20 | 20 |
| Toleuen | 38 | 38 | 38 | 38 | 38 | 38 | 38 | 38 | 38 | 38 | 40 | 40 |

[i]Polycaprolactone, product of Daicel Chemical Industries.
[ii]Ethylcellulose, product of Hercules.

TABLE 11

| Amount (g) | Comparative Exmaples | | | | | | | |
|---|---|---|---|---|---|---|---|---|
| | 3-1 | 3-2 | 3-3 | 3-4 | 3-5 | 3-6 | 3-7 | 3-8 |
| Lipase* | — | — | — | — | 2 | — | 2 | — |
| Cellulase* | — | — | — | — | — | 2 | — | — |
| Protease* | — | — | — | — | — | — | — | 2 |
| Placcel H4[i] | 40 | — | — | — | 40 | — | — | — |
| Ethylcellulose N-22[ii] | — | 40 | — | — | — | 40 | — | — |
| Alkyd resin a | — | — | 40 | — | — | — | 40 | — |
| Polyamino acid resin a | — | — | — | 40 | — | — | — | 40 |
| Caprous oxide | 20 | 20 | 20 | 20 | 20 | 20 | 20 | 20 |
| Toluene | 40 | 40 | 40 | 40 | 38 | 38 | 38 | 38 |

[i]Polycaprolactone, product of Daicel Chemical Industries.
[ii]Ethylcellulose, product of Hercules.
*Enzyme not yet coated with any lipid.

Paint film evaluation for antifouling activity

The evaluation method for antifouling activity mentioned above was repeated to obtain results as shown in Table 12 and Table 13.

Evaluation for paint film consumption

The cntifouling paint-coated steel panels were prepared as the same manner as Examples 3-1 to 3-12 and Comparative Examples 3-1 to 3-8. These were set on a drum rotor and rotated for 2 and 4 months in rate of 10 knots. The film thickness was measured by a surface analyzer to caluculate paint film consumption thickness ($\mu$m). The results are shown in Table 14 and Table 15.

Paint stability evaluation

Paint stability evaluation was carried out as the same manner mentioned above with the paint composition of Example 3-1 and that of Comparative Example 3-5. The results are shown in Table 16.

TABLE 12

| Immersion period | Fouling (%) | | | | | | | | | | | |
|---|---|---|---|---|---|---|---|---|---|---|---|---|
| | Example | | | | | | | | | | | |
| (months) | 3-1 | 3-2 | 3-3 | 3-4 | 3-5 | 3-6 | 3-7 | 3-8 | 3-9 | 3-10 | 3-11 | 3-12 |
| 2 | 0 | 0 | 0 | 0 | 0 | 0 | 0 | 0 | 0 | 0 | 0 | 0 |
| 4 | 0 | 0 | 0 | 0 | 0 | 0 | 0 | 0 | 0 | 0 | 0 | 0 |
| 6 | 0 | 0 | 0 | 0 | 0 | 0 | 0 | 0 | 0 | 0 | 0 | 0 |
| 12 | 0 | 0 | 0 | 0 | 0 | 0 | 0 | 0 | 0 | 0 | 0 | 0 |

TABLE 13

| Immersion period | Fouling (%) | | | | | | | | |
|---|---|---|---|---|---|---|---|---|---|
| | Comparative Example | | | | | | | | |
| (months) | 3-1 | 3-2 | 3-3 | 3-4 | 3-5 | 3-6 | 3-7 | 3-8 | Control |
| 2 | 5 | 5 | 5 | 10 | 5 | 5 | 5 | 5 | 50 |
| 4 | 10 | 10 | 10 | 10 | 5 | 10 | 10 | 10 | 70 |
| 6 | 20 | 20 | 25 | 25 | 15 | 15 | 20 | 20 | 100 |
| 12 | 60 | 55 | 60 | 60 | 60 | 60 | 65 | 60 | 100 |

TABLE 14

| Test period | Paint film consumption (μm) Example | | | | | | | | | | | |
|---|---|---|---|---|---|---|---|---|---|---|---|---|
| (months) | 3-1 | 3-2 | 3-3 | 3-4 | 3-5 | 3-6 | 3-7 | 3-8 | 3-9 | 3-10 | 3-11 | 3-12 |
| 2 | 25 | 9 | 10 | 17 | 23 | 11 | 9 | 10 | 10 | 11 | 14 | 9 |
| 4 | 47 | 19 | 19 | 36 | 40 | 21 | 17 | 18 | 19 | 20 | 29 | 18 |

TABLE 15

| Test period | Paint film consumption (μm) Comparative Example | | | | | | | |
|---|---|---|---|---|---|---|---|---|
| (months) | 3-1 | 3-2 | 3-3 | 3-4 | 3-5 | 3-6 | 3-7 | 3-8 |
| 2 | 2 | 1 | 2 | 1 | 3 | 3 | 2 | 2 |
| 4 | 4 | 4 | 4 | 3 | 5 | 5 | 4 | 4 |

TABLE 16

| | Example 3-1 | | Comparative Example 3-5 | |
|---|---|---|---|---|
| Storage period (months) | Fouling (%/12 months) | Paint film consumption (μm/2 months) | Fouling (%/12 months) | Paint film consumption (μm/2 months) |
| 1 | 0 | 25 | 60 | 3 |
| 3 | 0 | 24 | 65 | 2 |
| 6 | 0 | 25 | 70 | 2 |

We claim:

1. An antifouling paint composition which comprises a lipid-coated enzyme being stable in organic solvents as a result of coating with a lipid having 6 to 30 carbon atoms, and a paint resin.

2. The antifouling paint composition according to claim 1, wherein said lipid has a hydrophilic moiety selected from the group consisting of sugar residues, phosphoric acid groups, sulfonic acid groups and ammonium salt groups.

3. The antifouling paint composition according to claim 2, wherein said lipid is a glucoxide derivative for enzyme modification represented by the following general formula (1)

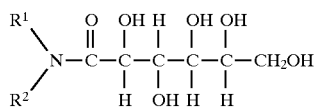

wherein $R^1$ and $R^2$ each independently represents a hydrocarbon group having 6 to 20 carbon atoms.

4. The antifouling paint composition according to claim 2, wherein said lipid-coated enzyme is a proteolytic enzyme or a polysaccharide decomposing enzyme, coated with a lipid.

5. The antifouling paint composition according to claim 2, wherein said paint resin is an enzyme-susceptible resin and said lipid-coated enzyme is capable of degrading said enzyme-susceptible resin, said antifouling paint composition thus being a self-polishing antifouling paint composition.

6. The antifouling paint composition according to claim 5, wherein said enzyme-susceptible resin is a polyester resin.

7. The antifouling paint composition according to claim 5, wherein said enzyme-susceptible resin is an alkyd resin.

8. The antifouling paint composition according to claim 5, wherein said enzyme-susceptible resin is a polylactone and said enzyme is a lipase.

9. The antifouling paint composition according to claim 5, wherein said enzyme-susceptible-resin is a polyamino acid resin.

10. The antifouling paint composition according to claim 5, wherein said enzyme-susceptible resin is a resin comprising a natural polysaccharide and/or a derivative thereof.

11. The antifouling paint composition according to claim 5, wherein said enzyme-susceptible resin is cellulose and/or a derivative thereof and said enzyme is a cellulase.

12. The antifouling paint composition according to claim 5, wherein said lipid is a glucoxide derivative for enzyme modification represented by the following general formula (1)

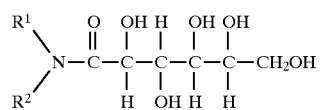

wherein $R^1$ and $R^2$ each independently represents a hydrocarbon group having 6 to 20 carbon atoms.

* * * * *